United States Patent [19]

Katsura

[11] Patent Number: 5,026,525
[45] Date of Patent: Jun. 25, 1991

[54] EXTRACORPOREAL BLOOD CIRCULATING APPARATUS

[75] Inventor: Yoshiro Katsura, Fuji, Japan

[73] Assignee: Terumo Kabushiki Kaisha, Tokyo, Japan

[21] Appl. No.: 195,884

[22] Filed: May 19, 1988

[30] Foreign Application Priority Data

May 19, 1987 [JP] Japan .................. 62-122243
Dec. 25, 1987 [JP] Japan .................. 62-331480

[51] Int. Cl.$^5$ ............................................. A61M 1/14
[52] U.S. Cl. ........................ 422/45; 128/DIG. 3; 261/DIG. 28
[58] Field of Search .................. 422/44-48; 128/DIG. 3; 261/DIG. 28

[56] References Cited

U.S. PATENT DOCUMENTS

| | | | |
|---|---|---|---|
| 2,847,008 | 8/1958 | Taylor et al. | 422/45 |
| 3,492,991 | 2/1970 | Dyer, Jr. | 422/44 X |
| 4,073,622 | 2/1978 | Luppi | 422/47 |
| 4,176,156 | 11/1979 | Asanuma et al. | 422/44 X |
| 4,469,659 | 9/1984 | Carson et al. | 422/46 |
| 4,493,692 | 1/1985 | Reed | 128/DIG. 3 |

FOREIGN PATENT DOCUMENTS 0103899 3/1984 European Pat. Off. .

Primary Examiner—Robert J. Warden
Assistant Examiner—Lynn M. Kummert
Attorney, Agent, or Firm—Burns, Doane, Swecker & Mathis

[57] ABSTRACT

An extracorporeal blood circulating apparatus includes an artificial lung and a blood reservoir which are joined to each other, and a blood inlet port for delivering blood from the artificial lung into the blood reservoir. The blood inlet port is defined in the same plane as that of a bottom of the blood reservoir and lying horizontally.

10 Claims, 3 Drawing Sheets 5,026,525

EXTRACORPOREAL BLOOD CIRCULATING APPARATUS

BACKGROUND OF THE INVENTION

The present invention relates to an extra-corporeal blood circulating apparatus, and more particularly to an extracorporeal blood circulating apparatus for exchanging gases in blood with an artificial lung, then delivering the blood into a blood reservoir from blood inlet ports which open at the bottom of the blood reservoir and lie horizontally, storing the blood temporarily in the blood reservoir, and thereafter supplying the stored blood to a human body.

When a thoracic operation, for example, is to be carried out on a patient, an extracorporeal blood circulating circuit is established using an artificial lung in which the blood is circulated for an exchange of carbon dioxide and oxygen. The blood is controlled at a prescribed temperature by a heat exchanger, and thereafter the gases are exchanged in the artificial lung. Then, the blood is temporarily stored in a blood reservoir for a steady supply of the blood. The blood is pumped into the patient under the operation at a constant pulse rate.

Blood reservoirs for use in extracorporeal blood circulation include a closed-type blood reservoir in the form of a soft bag for storing blood in an airtight condition and an open-type blood reservoir in the form of a hard housing for storing blood. The open-type blood reservoir is advantageous in that priming and confirmation of the stored amount of blood can easily be performed, and it would be easy to construct the blood reservoir as a unitary component of an artificial lung. Therefore, various extracorporeal blood circulating apparatus employing open-type blood reservoirs have been proposed.

FIG. 1 of the accompanying drawings schematically illustrates a extracorporeal blood circulating apparatus proposed by the applicant. The extracorporeal blood circulating apparatus comprises an artificial lung 2 and a blood reservoir 4 as an interconnected unitary system. The extracorporeal blood circulating apparatus is connected to the body of a patient through a pump (not shown) which supplies blood at a certain pulse rate. Blood B discharged from the human body is introduced into a heat exchanger and controlled at a prescribed temperature by warm or cold water. Thereafter, the blood B is fed from a blood supply port 6 into the artificial lung 2. The artificial lung 2 contains a multiplicity of hollow filamentary membranes 10 through which a gas A containing oxygen supplied from a gas inlet port 8 flows. The blood B, while passing around the hollow filamentary membranes, receives oxygen from the gas A and discharges carbon dioxide, and then flows upwardly through the artificial lung 2. The blood B then overflows the upper end of the artificial lung 2 into the blood reservoir 4 and is stored therein. After the exchange of oxygen and carbon dioxide, the gas A is discharged from the artificial lung 2 through a gas outlet port 12. The blood B stored in the blood reservoir 4 is supplied from a blood outlet port 14 into the human body.

SUMMARY OF THE INVENTION

It is a primary object of the present invention to provide an extracorporeal blood circulating apparatus for achieving a smooth influx of blood into a blood reservoir by allowing the blood, after a gas exchange in an artificial lung, to overflow blood inlet ports which open at the bottom of the blood reservoir in the same plane as that of the bottom and which lie horizontally, and for storing a minimum amount required of blood, the apparatus being compact in size.

Another object of the present invention is to provide an extracorporeal blood circulating apparatus comprising an artificial lung and a blood reservoir which are joined to each other, and a blood inlet port for delivering blood from the artificial lung into the blood reservoir, the blood inlet port being defined in the same plane as that of a bottom of the blood reservoir and lying horizontally.

Still another object of the present invention is to provide an extracorporeal blood circulating apparatus wherein the blood inlet port progressively spreads toward the bottom of the blood reservoir.

Yet still another object of the present invention is to provide an extracorporeal blood circulating apparatus wherein the bottom of the blood reservoir is slanted smoothly from an uppermost area toward a lowermost area, the blood inlet port being defined in the uppermost area of the bottom.

A further object of the present invention is to provide an extracorporeal blood circulating apparatus further including a blood dispersing member mounted in the blood inlet port for smoothing the flow of the blood.

A still further object of the present invention is to provide an extracorporeal blood circulating apparatus wherein the blood dispersing member comprises a mesh screen.

The above and other objects, features and advantages of the present invention will become more apparent from the following description when taken in conjunction with the accompanying drawings in which a preferred embodiment of the present invention is shown by way of illustrative example.

DETAILED DESCRIPTION OF THE PREFERRED EMBODIMENT

Figure 1:
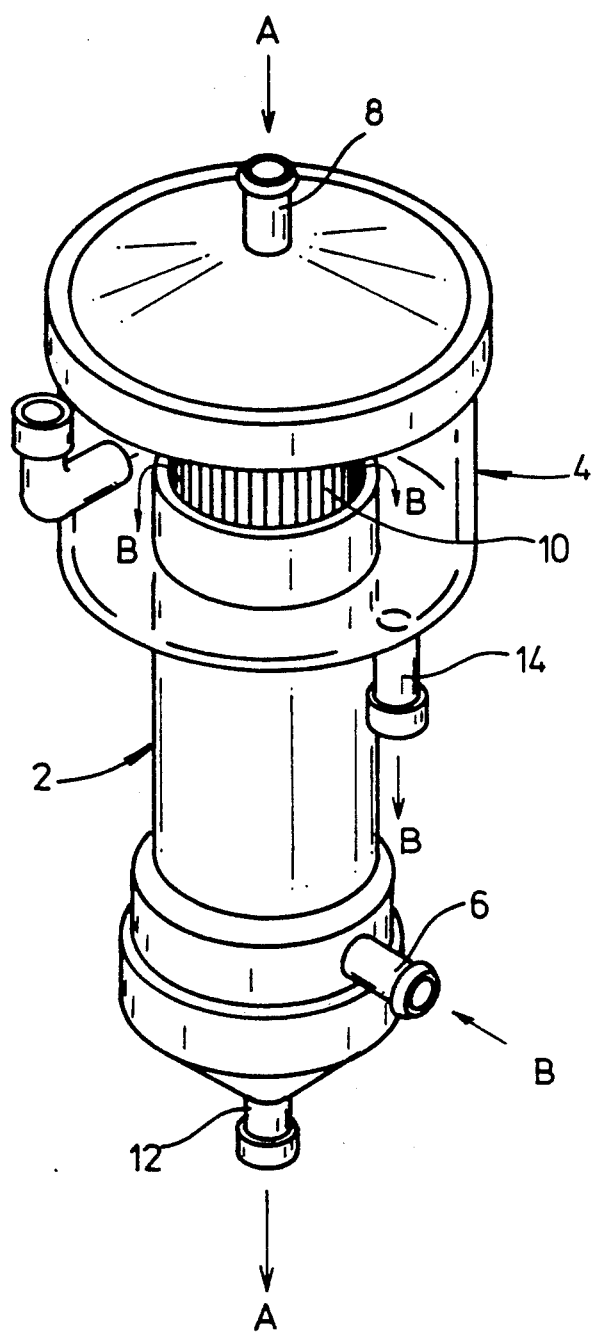
FIG. 1 is a schematic perspective view of a extracorporeal blood circulating apparatus shown as a comparative example.
Figure 2:
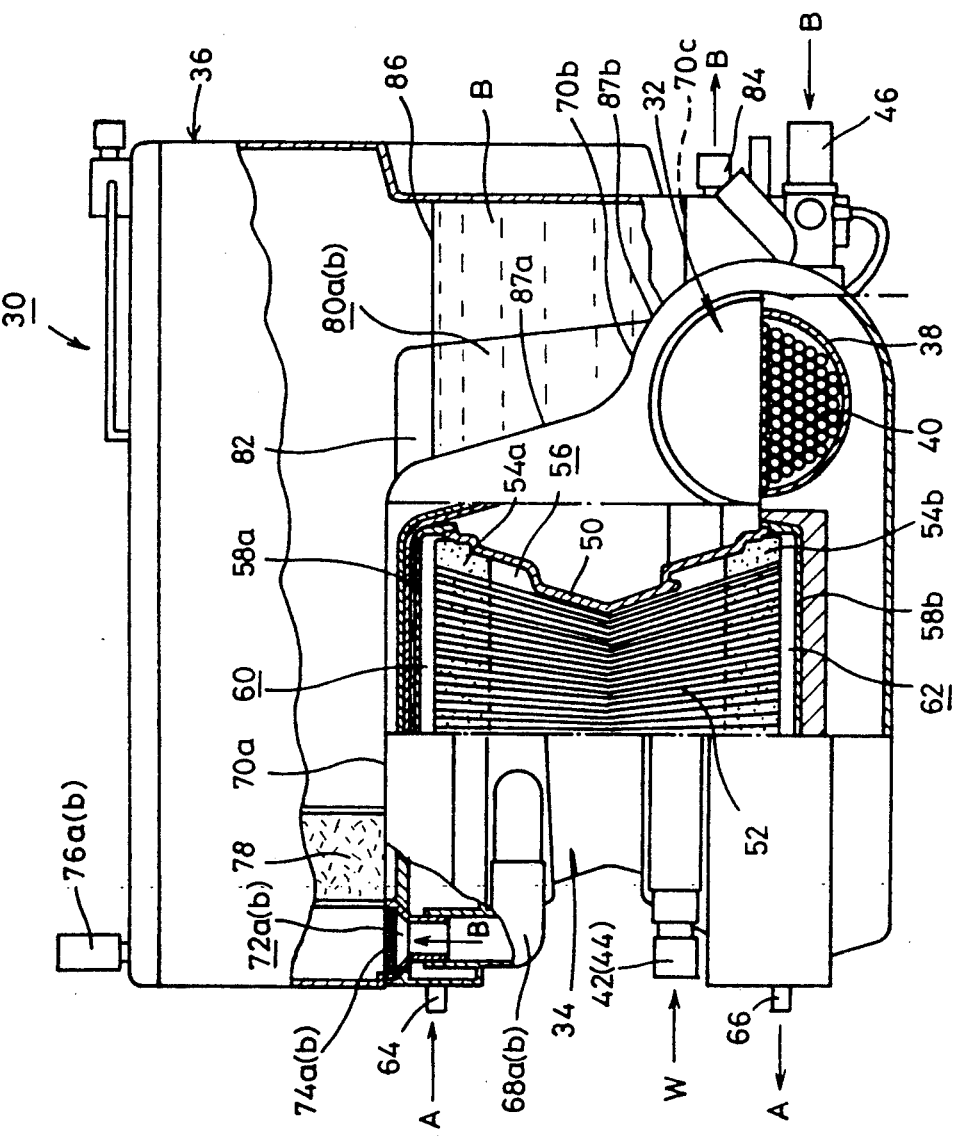
FIG. 2 is a schematic elevational view, partly in cross section, of a extracorporeal blood circulating apparatus according to the present invention.
Figure 3:
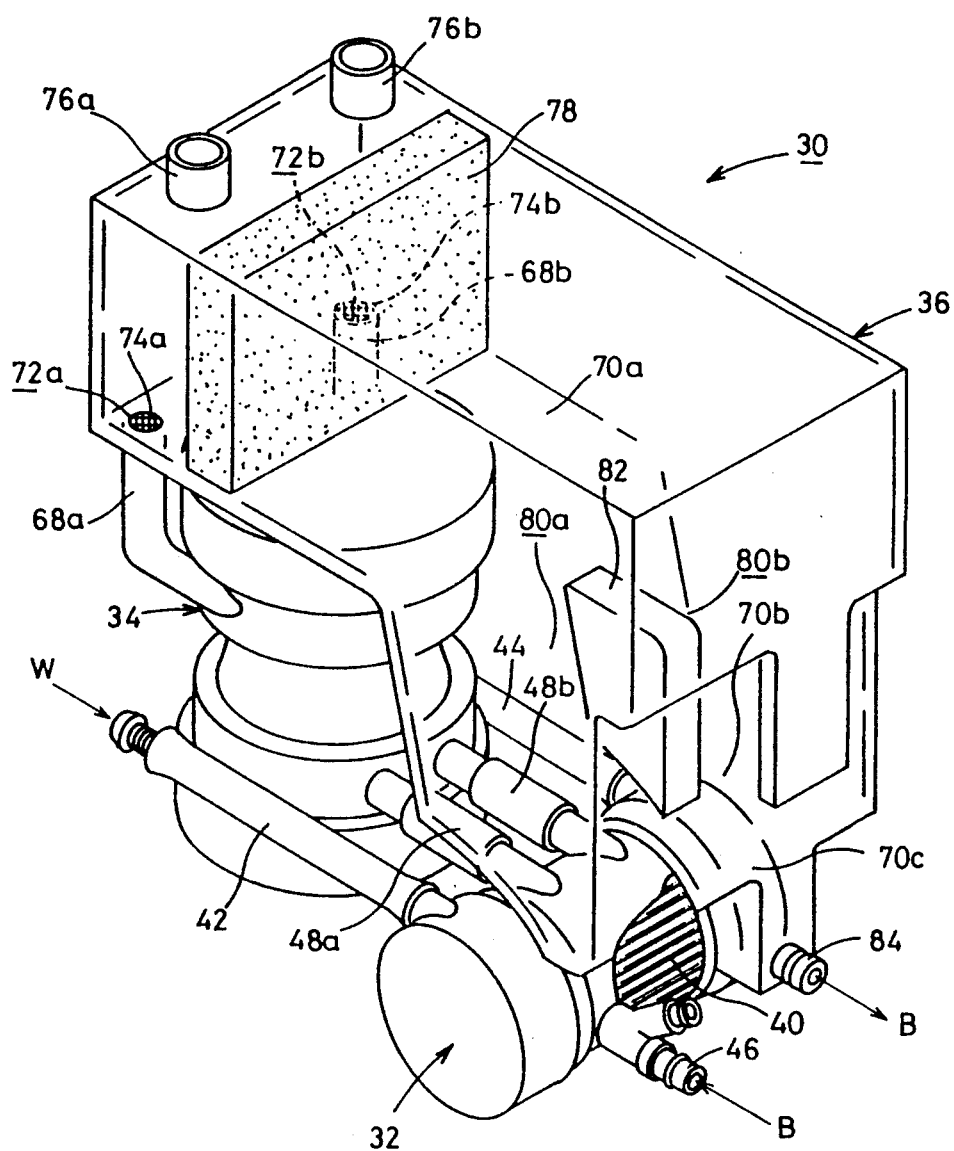
FIG. 3 is a schematic perspective view of the extracorporeal blood circulating apparatus illustrated in FIG. 2.

As shown in FIGS. 2 and 3, an extracorporeal blood circulating apparatus according to the present invention has a unitary apparatus assembly 30 comprising a heat exchanger 32, an artificial lung 34, and an open-type blood reservoir 36.

The heat exchanger 32 includes a tubular housing 38 accommodating therein a number of heat exchanger pipes 40. Warm or cold water W is supplied from a water port 42 to the pipes 40, and then discharged from the pipes 40 via a water port 44. Blood B flowing from a blood supply port 46 into the heat exchanger 32 is heated or cooled to a prescribed temperature while it is passing around the pipes 40. Thereafter, the blood B is supplied via two joint tubes 48a, 48b (see FIG. 3) to the artificial lung 34.

The artificial lung 34 serves to remove carbon dioxide from the blood B and add oxygen to the blood B. The artificial lung 34 includes a multiplicity of hollow filamentary membranes 52 bundled and stored in a substantially cylindrical housing 50 with a constricted central portion. On the upper and lower ends of the housing 50, there are mounted partitions 54a, 54b holding the opposite ends of the hollow filamentary membranes 52. The housing 50 and the partitions 54a, 54b jointly define a space surrounded thereby and housing the hollow filamentary membranes 52 therein, the space having a lower end communicating with the heat exchanger 32 through the joint tubes 48a, 48b. This space serves as a gas exchanging chamber 56 through which the blood B flows. Covers 58a, 58b are also mounted on the upper and lower ends of the housing 50. The partition 54a and the cover 58a define a gas supply chamber 60 therebetween, and the partition 54b and the cover 58b define a gas discharge chamber 62 therebetween. The hollow filamentary membranes 52 are supplied with a gas A containing oxygen from a gas inlet port 64 via the gas supply chamber 60. The gas A delivered from the hollow filamentary membranes 52 is discharged through the gas discharge chamber 62 from a gas outlet port 66.

The gas exchanging chamber 56 in the artificial lung 34 has an upper end communicating with the blood reservoir 36 through two L-shaped joint tubes 68a, 68b each having a horizontal portion extending from the gas exchanging chamber 56 and a vertical portion extending upwardly from the end of the horizontal portion over a certain length, the vertical portion having a spreading or flaring end. The blood reservoir 36 has a bottom plate composed of first through third steps 70a, 70b, 70c. The joint tubes 68a, 68b have blood inlet ports 72a, 72b, respectively, at their flaring ends, opening at the first uppermost step 70a on its lateral sides through blood dispersing mesh screens 74a, 74b, respectively, for smoothing the blood flow flowing therethrough. The blood inlet ports 72a, 72b open in the same plane as that of the first step 70a and lie horizontally. The blood reservoir 36 is made of a transparent plastic material. The blood reservoir 36 has a pair of drug inlet ports 76a, 76b above the blood inlet ports 72a, 72b, respectively, for adding various drugs such as a vasodilatator drug, an anticoagulant, and the like to the blood B.

A urethane anti-foaming member 78 is disposed on the first step 70a of the blood reservoir 36 near the blood inlet ports 72a, 72b. A partition 82 is mounted substantially centrally on the second step 70b and divides the blood storage space on the second step 70b into a first blood storage region 80a and a second blood storage region 80b for preventing the blood surface from being subjected to resonant vibration. The third lowermost step 70c is coupled to a blood outlet port 84 for supplying the blood B stored in the blood reservoir 36 into the human body. In operation, the blood outlet port 84 is coupled to the human body through a pump (not shown) which delivers the blood at a prescribed pulse rate. In the case, the pump may be a rotary type or peristaltic finger type. The first through third steps 70a through 70c are smoothly joined by slanted surfaces 87a, 87b.

The extracorporeal blood circulating apparatus of the present invention is basically of the above structure. Now, operation and advantages of the extracorporeal blood circulating apparatus will be described below.

The blood B coming from the blood supply port 46 is supplied through the gaps between the tubes 40 stored in the heat exchanger 32 to the artificial lung 34. At this time, water W maintained at a prescribed temperature is flowing through the heat exchanger tubes 40 through the water ports 42, 44. The blood B is heated or cooled to a predetermined temperature by the water W flowing through the tubes 40.

The blood B fed from the heat exchanger 32 via the joint tubes 48a, 48b into the artificial lung 34 enters the gas exchanging chamber 56 surrounded by the housing 50 in which oxygen is added to the blood B and carbon dioxide is removed from the blood B. More specifically, the gas A containing oxygen is supplied into the bundled hollow filamentary membranes 52 in the housing 50 from the gas inlet port 64 through the gas supply chamber 60. Oxygen and carbon dioxide are exchanged in the blood B through the hollow filamentary membranes 52. The gas A containing carbon dioxide is discharged via the gas discharge chamber 62 from the gas outlet port 66.

The blood B to which oxygen has been added in the artificial lung 34 then flows through the joint tubes 68a, 68b and the blood inlet ports 72a, 72b into the blood reservoir 36. As described above, the blood inlet ports 72a, 72b at the ends of the joint tubes 68a, 68b are spread and open in the same plane as that of the first step 70a of the bottom of the blood reservoir 36. Since the stream of the blood B that has reached the spreading blood inlet ports 72a, 72b increases in its cross-sectional area, the speed of flow of the blood B is reduced. Moreover, since the blood inlet ports 72a, 72b are defined in the same plane as that of the first step 70a, the blood B coming out of the blood inlet ports 72a, 72b flows with suppressed energy into the blood reservoir 36. Therefore, the blood B does not gush, but flows moderately into the blood reservoir 36. Then, the blood B passes through the urethane anti-foaming member 78 and then along the slanted surfaces 87a, 87b, so that the blood B is quietly stored in the blood reservoir 36.

The joint tubes 68a, 68b are of the L shape including a horizontal portion extending from the upper end of the gas exchanging chamber 56 and a vertical portion extending upwardly from the horizontal portion over a certain length. Therefore, the blood B flowing out of the gas exchanging chamber 56 under the pressure developed by the pump (not shown) or the blood head produced by the higher human body position flows upwardly through the L-shaped joint tubes 68a, 68b, during which time the kinetic energy of the blood B is reduced by an increase in the potential energy thereof, thereby resulting in a reduction in the speed of flow of the blood B. As a consequence, the blood B is allowed to flow smoothly into the blood reservoir 36. Inasmuch as the blood inlet ports 72a, 72b are positioned at a location higher than the gas exchanging chamber 56 in the artificial lung 34, no air would flow from the blood inlet ports 72a, 72b into the gas exchanging chamber 56 when the pump is stopped. As the blood inlet ports 72a, 72b are defined in the same plane as that of the first step 70a, the amount of blood stored in the assembly 30, i.e., the amount of blood outside of the patient's body, can be reduced, and hence the physical burdon on the patient can be lowered.

The blood B stored in the blood reservoir 36 is then intermittently or pulsatively delivered out to the human body by the pump (not shown) coupled to the blood outlet port 84. The surface level 86 of the blood B stored in the blood reservoir 36 would be subjected to resonant vibration due to intermittent delivery of the blood B by the pump. However, such resonant vibration is highly effectively be suppressed by the partition 82 on the second step 70b in the blood reservoir 36. More specifically, the partition 82 located in the blood reservoir 36 is effective in making the system natural frequency widely different from the pulse rate of the pump, thus suppressing the undesirable resonant vibration. Since the fluctuation of the surface level 86 arising from the pulse rate of the pump is small, the height of the surface level 86, i.e., the amount of the blood B stored in the blood reservoir 36 can easily and accurately be checked by a visual inspection. Moreover, inasmuch as any turbulent motion of the blood B in the blood reservoir 36 is effectively suppressed, vibration of the blood B is held to a minimum, and no unwanted vibration is applied to the apparatus.

With the present invention, as described above, the extracorporeal blood circulating apparatus includes the artificial lung and the blood reservoir which are joined to each other, and the blood flowing out of the artificial lung is caused to flow through the blood inlet ports having spreading ends which open in the same plane as that of the bottom of the blood reservoir and which lie horizontally, into the blood reservoir. The blood flowing out of the artificial lung reduces its speed of travel at the spreading ends of the blood inlet ports. Because the blood inlet ports are defined in the same plane as that of the bottom of the blood reservoir and lie horizontally, the blood does not gush, but flows moderately or quietly into the blood reservoir. Since the blood inlet ports do not project on the bottom of the blood reservoir, the amount of blood in the apparatus is a minimum that is required, and hence the amount of blood which needs to flow outside of the patient is reduced.

The present invention is not limited to the illustrated embodiment, but the principles of the invention are also applicable to a extracorporeal blood circulating apparatus which is separate from a heat exchanger, for example.

Although a certain preferred embodiment has been shown and described, it should be understood that many changes and modifications may be made therein without departing from the scope of the appended claims.

What is claimed is:

1. An extracorporeal blood circulating apparatus comprising an artificial lung and a blood reservoir which are joined to each other by at least one tube and a blood inlet port for delivering blood from said artificial lung into said blood reservoir, said blood inlet port being further defined in the same plane as that of a bottom of said blood reservoir and lying horizontally, the bottom of said blood reservoir comprising step portions joined by smoothly slanted surfaces, thereby defining a smoothly curved surface extending from an uppermost step portion toward a lowermost step portion, said blood inlet port being defined in said uppermost step portion of the bottom of said blood reservoir.

2. An extracorporeal blood circulating apparatus according to claim 1, wherein said blood inlet port progressively spreads toward the bottom of said blood reservoir.

3. An extracorporeal blood circulating apparatus according to claim 1, further including a blood dispersing member mounted in said blood inlet port for smoothing the flow of the blood.

4. An extracorporeal blood circulating apparatus according to claim 3, wherein said blood dispersing member comprises a mesh screen.

5. An extracorporeal blood circulating apparatus according to claim 1, wherein said blood inlet port comprises a flared opening spreading progressively upwardly toward the bottom of said blood reservoir.

6. An extracorporeal blood circulating apparatus comprising:
a blood reservoir having a bottom plate;
an artificial lung positioned below at least a portion of said bottom plate;
at least one tube having a first end fluidly connected to an interior of the artificial lung at an upper end of the artificial lung and having a second oppositely positioned end; and
means for providing smooth blood flow into the blood reservoir from the artificial lung and for substantially preventing gushing of the blood into the blood reservoir, said means including at least one blood inlet port connected to said bottom plate and to the second end of said at least one tube for fluidly communicating the at least one tube with an interior of the blood reservoir, an end of the blood inlet port which is connected to said bottom plate being flared outwardly away from a longitudinal axis of the blood inlet port, an inner surface of said bottom plate which faces toward the interior of the blood reservoir including a first step portion, a second step portion connected to the first step portion by a smoothly extending surface, and a third step portion connected to the second step portion by a smoothly extending surface, said blood inlet port opening into the first step portion.

7. The extracorporeal blood circulating apparatus according to claim 6, wherein the portion of the tube adjacent its second end is positioned substantially vertically.

8. The extracorporeal blood circulating apparatus according to claim 7, wherein said first step portion is positioned vertically higher than said second step portion and said third step portion.

9. The extracorporeal blood circulating apparatus according to claim 7, wherein the portion of said tube located adjacent its first end is positioned substantially horizontally.

10. The extracorporeal blood circulating apparatus according to claim 6, including a second tube having a first end fluidly connected to the upper end of the artificial lung and an oppositely located second end, and wherein said means for providing smooth blood flow includes a second blood inlet port connected to the bottom plate and to the second end of the second tube, an end of the second blood inlet port which is connected to the bottom plate being flared outwardly away from a longitudinal axis of the second blood inlet port.

* * * * *